United States Patent
Choi et al.

(10) Patent No.: US 10,392,715 B2
(45) Date of Patent: Aug. 27, 2019

(54) ELECTROCHEMICAL REDUCTIVE AMINATION OF FURFURAL-BASED MOLECULES

(71) Applicant: Wisconsin Alumni Research Foundation, Madison, WI (US)

(72) Inventors: Kyoung-Shin Choi, Fitchburg, WI (US); John James Roylance, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 60 days.

(21) Appl. No.: 15/249,898

(22) Filed: Aug. 29, 2016

(65) Prior Publication Data

US 2018/0057949 A1    Mar. 1, 2018

(51) Int. Cl.
| | |
|---|---|
| *C25B 3/00* | (2006.01) |
| *C25B 3/04* | (2006.01) |
| *C25B 11/04* | (2006.01) |
| *C07D 307/52* | (2006.01) |
| *C07D 307/68* | (2006.01) |

(52) U.S. Cl.
CPC .............. *C25B 3/04* (2013.01); *C07D 307/52* (2013.01); *C07D 307/68* (2013.01); *C25B 11/04* (2013.01)

(58) Field of Classification Search
CPC ........................................................ C25B 3/04
USPC .................... 205/431, 435, 438, 427, 436
See application file for complete search history.

(56) References Cited

U.S. PATENT DOCUMENTS

| | | | |
|---|---|---|---|
| 5,919,349 A | * | 7/1999 | Huber ................. C25B 3/04 204/292 |
| 7,052,587 B2 | | 5/2006 | Gibson et al. |
| 9,061,961 B2 | | 6/2015 | Kubanek et al. |
| 2011/0108432 A1 | | 5/2011 | Malkowsky et al. |
| 2012/0271060 A1 | | 10/2012 | Munoz de Diego et al. |
| 2014/0110268 A1 | * | 4/2014 | Jackson ............. C25B 11/0415 205/351 |
| 2014/0235838 A1 | | 8/2014 | Stahl et al. |
| 2015/0060296 A1 | | 3/2015 | Elangovan et al. |
| 2015/0361566 A1 | | 12/2015 | Choi et al. |
| 2016/0032469 A1 | | 2/2016 | Magalhaes Mendes et al. |
| 2016/0201204 A1 | | 7/2016 | Choi et al. |
| 2016/0237576 A1 | | 8/2016 | Choi et al. |

FOREIGN PATENT DOCUMENTS

WO    WO2015137914    9/2015

OTHER PUBLICATIONS

Simion et al., "Synthesis of Imines, Diimines and Macrocyclic Diimines as Possible Ligands, in Aqueous Solutions," J. Chem. Soc., Perkin Trans. 1 (no month, 2001), pp. 2071-2078. (Year: 2001).*

(Continued)

*Primary Examiner* — Edna Wong
(74) *Attorney, Agent, or Firm* — Bell & Manning, LLC; Michelle Manning

(57) ABSTRACT

Electrochemical cells for the reductive amination of furfural-based molecules are provided. Also provided are methods of using the electrochemical cells to carry out the electrochemical reductive amination reactions. Using the cells and methods, furfural-based molecules can be converted into amines via the conversion of their formyl groups to amine groups.

24 Claims, 3 Drawing Sheets

(56) References Cited

OTHER PUBLICATIONS

Nilges et al., "Electrochemistry for Biofuel Generation: Production of Furans by Electrocatalytic Hydrogenation of Furfurals," Energy Environ. Sci. (no month, 2013), vol. 6, pp. 2925-2931. (Year: 2013).*

Simion et al., "Synthesis of Imines, Diimines and Macrocyclic Diimines as Possible Ligands, in Aqueous Solutions," J. Chem. Soc., Perkin Trans. 1 (2001), pp. 2071-2078. (Year: 2001).*

Nilges et al., "Electrochemistry for Biofuel Generation: Production of Furans by Electrocatalytic Hydrogenation of Furfurals," Energy Environ. Sci. (2013), vol. 6, pp. 2925-2931. (Year: 2013).*

Chen et al., Electro-Generation of Furfural Alcohol in Ni-P-mCMC/mCS Bipolar Membrane Equipped Electrolysis Cell, Advanced Materials Research, vols. 287-290, Jul. 4, 2011, Trans Tech Publications, pp. 564-568.

Pienemann et al., Reductive Amination of Ketones and Aldehydes at the Mercury-Cathode, Communications, Nov. 1987, pp. 1005-1007.

Cvetovich et al., Novel Electrochemical Reductive Amination of 4-Oxo-5-O-(*tert*-butyldimethylsilyl) avermectin $B_1$, J. Org. Chem., vol. 62, No. 19, 1997, pp. 6697-6698.

Smirnov et al., Electrochemical Reductive Amination, Translated from Zhurnal Organicheskoi Khimii, vol. 28, No. 1, Jan. 1992, pp. 51-58.

H. Lund, Electroorganic Preparations, Acta Chemica Scandinavica 13, No. 2, 1959, pp. 249-267.

Xu et al., Direct reductive amination of 5-hydroxymethylfurfural with primary/secondary amines via Ru-complex catalyzed hydrogenation, RSC Adv. 4, Oct. 30, 2014, pp. 59083-59087.

Cukalovic, Production of biobased HMF derivatives by reductive amination, Green Chemistry 12, May 18, 2010, pp. 1201-1206.

Concialini et al., Diastereoselective Electrochemical Reductive Amination of 2,5-Hexanedione and 2,6-Heptanedione, English Abstract from Gazzetta chimica italiana, vol. 125, Issue 2, 1995, pp. 77-81.

Palmisano et al., Waste-Free Electrochemical Oxidation of Alcohols in Water, Adv. Synth. Catal. 348, 2006, pp. 2033-2037.

Chadderdon et al., Electrocatalytic oxidation of 5-hydroxymethylfurfural to 2,5-furandicarboxylic acid on supported Au and Pd bimetallic nanoparticles, Green Chem. 16, Apr. 24, 2014, pp. 3778-3786.

Kwon et al., Electrocatalytic Hydrogenation of 5-Hydroxymethylfurfural in the Absence and Presence of Glucose, ChemSusChem 6, Jul. 15, 2013, pp. 1659-1667.

Nilges et al., Electrochemistry for biofuel generation: production of furans by electrocatalytic hydrogenation of furfurals, Energy Environ. Sci. 6, Aug. 6, 2013, pp. 2925-2931.

Vuyyuru et al., Oxidation of biomass derived 5-hydroxymethylfurfural using heterogeneous and electrochemical catalysis, Catalysis Today 195, Jun. 8, 2012, pp. 144-154.

Presentation by John Roylance at job interview, Aug. 2014.

McDonald et al., A new electrochemical synthesis route for a BiOI electrode and its conversion to a highly efficient porous BiVO4 photoanode for solar water oxidation, Energy Environ. Sci. 5, 2012, pp. 8553-8557.

Seabold et al., Efficient and Stable Photo-Oxidation of Water by a Bismuth Vanadate Photoanode Coupled with an Iron Oxyhydroxide Oxygen Evolution Catalyst, J. Am. Chem.Soc. 134, Jan. 20, 2012, pp. 2186-2192.

Park et al., Progress in bismuth vanadate photoanodes for use in solar water oxidation, Chem. Soc. Rev. 42, Oct. 23, 2012, pp. 2321-2337.

Kim et al., Nanoporous $BiVO_4$ Photoanodes with Dual-Layer Oxygen Evolution Catalysts for Solar Water Splitting, Science 343, Feb. 28, 2014, pp. 990-994.

Wei et al., Photoelectrochemical Cell and Its Applications in Optoelectronics, Int. J. Electrochem. Sci., vol. 2, Oct. 20, 2007, pp. 897-912.

Hansen et al., Cu catalyzed oxidation of 5-hydroxymethylfurfural to 2,5-diformylfuran and 2,5-furandicarboxylic acid under benign reaction conditions, Applied Catalysis A: General 456, Feb. 21, 2013, pp. 44-50.

Bragd et al., TEMPO-mediated oxidation of polysaccharides: survey of methods and applications, Topics in Catalysis, vol. 27, Nos. 1-4, Feb. 2004, pp. 49-66.

International Search Report and Written Opinion mailed in PCT Application No. PCT/US16/12312, dated May 10, 2016.

Grabowski et al., The electrochemical oxidation of 5-hydroxymethylfurfural with the nickel oxide/hydroxide electrode, Electrochimica Acta, vol. 36. No. 13, 1991, pp. 1995.

Cha et al., Combined biomass valorization and hydrogen production in a photoelectrochemical cell, Nature Chemistry, vol. 7, Mar. 9, 2015, pp. 328-333.

Cottier et al., Oxidation of 5-Hyrodxymethylfurfural and Derivatives to Furanaldehydes with 2,2,6,6-Tetramethylpiperidine Oxide Radical—Co-oxidant Pairs, J. Heterocyclic Chem. (May-Jun. 1995), vol. 32, pp. 927-930.

Green et al., The Electrocatalytic Hydrogenation of furanic compounds in a continuous electrocatalytic membrane reactor, Green Chem., May 10, 2013, vol. 15, pp. 1869-1879.

Parpot et al., Electrochemical Investigations of the Oxidation-Reduction of Furfural in Aqueous Medium Application to Electrosynthesis, Electrochimica Acta, Oct. 9, 2003, vol. 49, pp. 397-403.

* cited by examiner

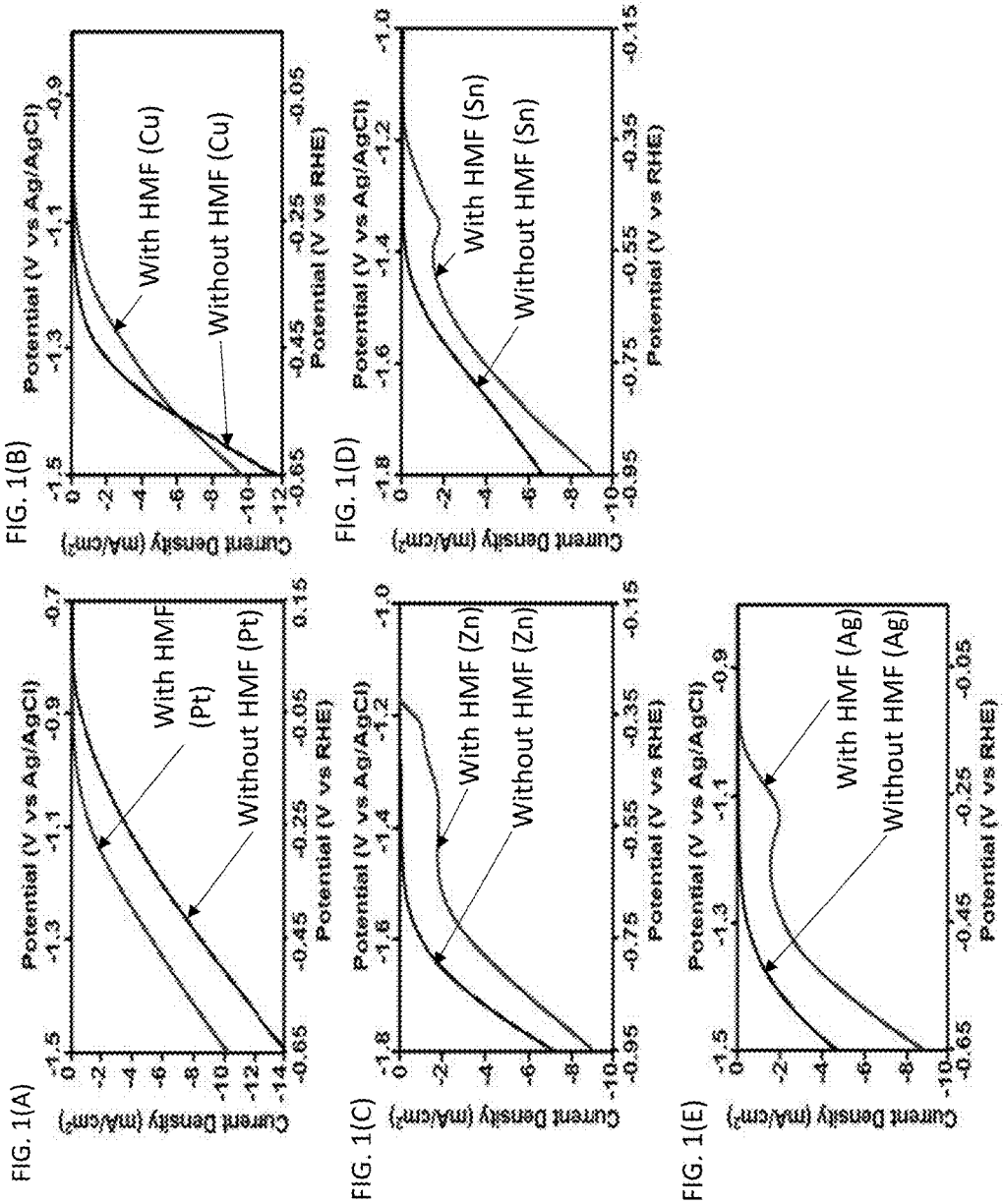

ELECTROCHEMICAL REDUCTIVE AMINATION OF FURFURAL-BASED MOLECULES

REFERENCE TO GOVERNMENT RIGHTS

This invention was made with government support under DE-SC0008707 awarded by the US Department of Energy. The government has certain rights in the invention.

BACKGROUND

With the ever increasing concern over fossil fuel supply, which has traditionally been the feedstock to produce a diverse range of goods including fuels, polymers, organic solvents, and even pharmaceutical compounds, research and development of biomass-based alternatives for fuels and commodity chemicals has gained significant attention. In the course of developing biomass-based alternatives, raw biomass is processed to a number of intermediates. 5-hydroxymethylfurfural (HMF) is one such intermediate that has been the subject of considerable attention. HMF is produced by dehydration of hexoses, such as glucose in cellulosic matter. Among the many reactions HMF may undergo (e.g. oxidation, reduction, etherification), reductive amination, which adds an amine group to a hydrocarbon framework, enables the synthesis of more diverse biomass-driven compounds including amine-based polymers (nylon) and pharmaceutical compounds.

Reductive amination of furfurals involves the conversion of the formyl group to an amine group, which is commonly accomplished in two steps as illustrated in Scheme 1. In this scheme the aldehyde is first converted to an aldimine (Step 1 in Scheme 1) by reaction with ammonia or a primary amine. Formation of the aldimine has traditionally utilized concentrated or liquid amine source and nonaqueous solvents. However, aldimine can also be formed in aqueous media under pH conditions where a large portion of ammonia or amine is present in its unprotonated form. The stability of aldimine is pH dependent and lowering pH can cause the hydrolysis of the aldimine back to aldehyde.

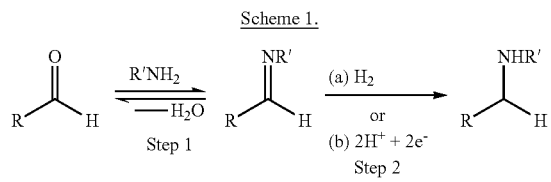

Scheme 1.

The second step of reductive amination is reduction of the aldimine to an amine by the hydrogenation of the C=N bond (Step 2 in Scheme 1). This process has commonly been achieved by using $H_2$ over Raney Ni or precious metal catalysts (e.g. Au, Ir, Pd, Pt, Rh, and Ru). Recent efforts have been made to utilize inexpensive alternatives, such as FeNi alloy catalysts. However, for this method $H_2$, which is a valuable fuel that must be generated from other primary energy sources, needs to be consumed. Hydrogenation can also be achieved by using a hydride (e.g., sodium borohydride, sodium cyanoborohydride, and sodium triacetoxyborohydride) or by using Zn powder as a reducing agent and water as the hydrogen source. These reactions, however, require the consumption of reducing agents, significant solution cleanup, and disposal of waste that can be toxic.

SUMMARY

Electrochemical cells for the reductive amination of furfural-based molecules are provided. Also provided are methods of using the electrochemical cells to carry out the electrochemical reductive amination reactions.

The electrochemical reductive aminations of furfural-based molecules can be carried out in an electrochemical cell comprising an aqueous electrolyte solution, a cathode (the electrode where reduction occurs), and an anode (the electrode where oxidation occurs), wherein the cathode and the anode are in electrical communication. The electrochemical cell can be either an undivided cell, in which case the cathode electrolyte and the anode electrolyte are not separated and thus identical, or a divided cell, in which case the cathode electrolyte solution is separated from the anode electrolyte solution by a divider such as a frit or a membrane. The methods of conducting the electrochemical amination of the furfural-based molecules comprise: combining the furfural-based molecules with a primary amine or ammonia in the aqueous cathode electrolyte solution, wherein the furfural-based molecules react with the primary amine or ammonia to form aldimine intermediate molecules; and creating a potential difference between the anode and the cathode to provide a flow of electrons from the anode to the cathode, wherein the electrons at the cathode and $H^+$ from water in the aqueous cathode electrolyte solution undergo reductive amination reactions with the aldimine intermediate molecules to form aminated molecules.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

FIG. 1(A) depicts a linear sweep voltammetry (LSV) curve of a Pt electrode in 0.7 M methylamine buffer solution (pH 11.0) with and without 0.02 M HMF (scan rate 5 mV $s^{-1}$). FIG. 1(B) depicts an LSV of a Cu electrode in 0.7 M methylamine buffer solution (pH 11.0) with and without 0.02 M HMF (scan rate 5 mV $s^{-1}$). FIG. 1(C) depicts an LSV of a Zn electrode in 0.7 M methylamine buffer solution (pH 11.0) with and without 0.02 M HMF (scan rate 5 mV $s^{-1}$). FIG. 1(D) depicts an LSV of a Sn electrode in 0.7 M methylamine buffer solution (pH 11.0) with and without 0.02 M HMF (scan rate 5 mV $s^{-1}$). FIG. 1(E) depicts an LSV of an Ag electrode in 0.7 M methylamine buffer solution (pH 11.0) with and without 0.02 M HMF (scan rate 5 mV $s^{-1}$).

DETAILED DESCRIPTION

Figure 2B:
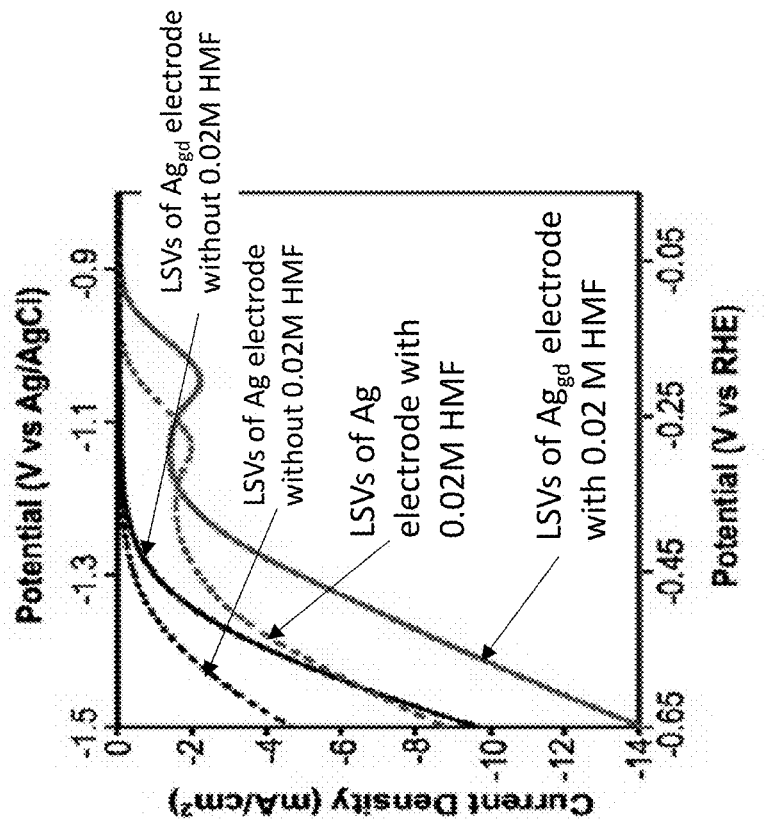
FIG. 2(B) shows LSVs of the $Ag_{gd}$ electrode with (solid) and without (dashed) 0.02 M HMF, compared with LSVs of an Ag electrode (black) with (solid) and without (dashed) 0.02M HMF in a 0.7 M methylamine buffer solution (pH 11.0) (scan rate 5 mV $s^{-1}$).

Electrochemical cells for the reductive amination of furfural-based molecules are provided. Also provided are methods of using the electrochemical cells to carry out the electrochemical reductive amination reactions. Using the cells and methods, furfural-based molecules can be converted into amines via the conversion of their formyl groups into amine groups. The electrolyte solution in the electrochemical cells may be substantially free of reducing agents and hydrogen sources other than the water, where an electrolyte solution can be considered "substantially free" of reducing agents or hydrogen sources if it does not contain any other chemical species whose primary function is to act as a reducing agent or hydrogen source, although there may be chemical species present that contribute to a minor extent in these functions.

As used herein, the term furfural-based molecules refers to molecules comprising a furfural group. The cells and methods are able to convert the furfural-based molecules, into organic building block amine compounds that are useful in the production of a variety of chemicals. Furfural itself (i.e., furan-2-carbaldehyde) is an example of a furfural-based molecule. HMF, a common biomass-derived intermediate, is another example of furfural-based molecule. Other furfural-based biomass-derived intermediates that can be reductively aminated using the present methods include HMF derivatives having different ring substituents, such as hydroxyl or alkyl substituents, including 5-methylfurfural (5-MF), 2,5-diformylfuran (DFF), and 5-formyl-2-furancarboxylic acid (FFCA).

The amindated furfural-based molecules that are formed by the electrochemical reductive amination of the furfural-based molecules have a variety of useful applications. For example, the amines can be used as monomers for the polymerization of amine-based polymers. By way of illustration, the 2-hydroxymethyl-5-(methylamninomethyl)furan produced via the electrochemical reductive amination of hydroxymethyl furfural can be used as a monomer for the polymerization of nylon, as described in PCT application publication number WO 2015/137914. The amindated furfural-based molecules may also have uses as pharmaceutical compounds or as starting materials for the synthesis of pharmaceutical compounds. See, for example, Cukalovic et al., *Green Chem.*, 2010, 12, 1201-1206. By way of illustration, some aminomethyl-hydroxymethylfuran derivatives, including those made from the reductive amination of HMF, are known to have pharmaceutical activities, as described in Xu et al., *RSC Adv.*, 2014, 4, 59083.

The reductions can be conducted in an aqueous electrolyte solution comprising the furfural-based molecules and a primary amine or ammonia under mild conditions at ambient temperatures and pressures (e.g., about 20° C. to about 25° C. and about 1 atm). The water of the aqueous solution can be used as the sole hydrogen source, without the need to include any additional hydrogen source, $H_2$ or hydrides. Even under these mild conditions, the reductive amination of the furfural-based molecules competes favorably with water reduction to provide reductive amination products with high selectivities. This is advantageous because the electrochemical reduction of the furfural-based molecules is thermodynamically more favorable than the reduction of water and because it eliminates inefficiencies related to the production, storage and use of $H_2$.

Primary amines that can be used as reactants in the electrochemical reductive aminations include aliphatic amines, such as methylamine and ethanolamine, and aromatic amines, such as aniline and aniline derivatives.

One embodiment of an electrochemical cell for carrying out the electrochemical reductive amination of the furfural-based molecules comprises a cathode, an anode, and an aqueous electrolyte comprising the furfural-based molecules and primary amines. Optionally, a reference electrode can be added to the cell to precisely control the potential applied to the cathode. The cathode, which is in electrical communication with the anode, comprises a material that is catalytically active for the reductive amination of the furfural-based molecules to amines. In embodiments of the methods in which the furfural-based molecules can be consumed by oxidation reactions at the anode, which would lower the efficiency for the cathode reaction undesirably, a divided cell can be used in which only the cathode compartment contains the furfural-based molecules. However, if the oxidation of the furfural-based molecules at the anode is not a concern, the reductive amination can be carried out in an undivided cell in which the anode and cathode are both submerged in the same aqueous electrolyte solution. Optionally, the solubility of the primary amines, the ammonia, and/or the furfural-based molecules can be enhanced by including additional organic solvents in the aqueous electrolyte solution.

The operation of the electrochemical cells is described in detail in the Example. A more general description of electrochemical reductive amination of furfural-based molecules in an aqueous electrolyte solution is provided here. To operate the electrochemical cell, a voltage source is used to create a potential difference between the anode and the cathode, such that a flow of electrons from the anode to the cathode through an external wire results. The electrons at the surface of the cathode then undergo reduction reactions with the furfural-based molecules in the aqueous electrolyte solution, while oxidation reactions occur at the anode. More specifically, in a first step, aldimine intermediates form via the reaction of the furfural-based molecules with the primary amine and/or ammonia in the aqueous cathode solution and, in a second step, the electrons and $H^+$ from the water hydrogenate the aldimine intermediates at the cathode to form the amines. This two-step process is shown using HMF and methylamine as reactants in Scheme 2.

The cathode materials should be catalytically active for the reductive amination of the aldimine intermediates to amines, which includes having good surface absorption properties for the aldimine intermediates and being a poor catalyst for the reduction of water, which competes with the reductive amination of the furfural-based molecules. In addition, the cathode materials are desirably non-toxic. Cathode materials that are catalytically active for the reductive amination of aldimine intermediates to aminated furfural-based molecules include silver, zinc, tin, copper, and indium. An example of a catalytically active cathode material that works well is silver having a dendritic fractal morphology, as shown in FIG. 2(A) and described in J. J. Roylance, T. W. Kim and K. S. Choi, *ACS Catal.*, 2016, 6, 1840-1847. Thus, cadmium, lead, and mercury electrodes are not necessary, nor are precious metal electrodes. The catalytically active material may be supported or unsupported. For example, the cathode may comprise a film or particles of the catalytically active material on a non-catalytic, but electrically conducting, substrate.

In order to achieve high selectivity, the electrochemical reductive aminations are desirably carried out in aqueous cathode electrolyte solutions at a pH that favors the unprotonated form of the primary amine over its protonated form or, if ammonia is used as the reactant, that favors ammonia over ammonium, since only the unprotonated form of the reactant will undergo aldimine formation. For the complete conversion of the furfural-based molecules to their aldimine forms using primary amines, the pH of the solution should be adjusted to generate the unprotonated form of the primary amine in an amount that is equal to or greater than the amount of furfural-based molecules. The relationship between the solution pH, the $pK_a$ of the protonated amine, and the concentrations of the protonated and unprotonated amine is shown below by the Herderson-Hasselbalch equation.

$$pH = pK_a + \log \frac{\text{molarity of unprotonated amine}}{\text{molarity of protonated amine}} \quad (1)$$

For example, using the present cells and methods, the complete reductive amination of 20 mM furfural-based molecules can be achieved with a 0.7 M methyl amine solution at a pH of 10 or higher (the $pK_a$ of the protonated methyl amine, $CH_3NH_3^+$, is ~10.6.) Similarly, for the complete conversion of the furfural-based molecules to their aldimine forms using ammonia, the pH of the solution should be adjusted to generate ammonia in an amount that is equal to or greater than the amount of furfural-based molecules. In general, the aldimine formation with ammonia is not as favored as the aldimine formation with primary amines. Therefore, when ammonia is used instead of primary amines, higher pH conditions or more concentrated ammonia solutions are required to convert the same amount of furfural-based molecules to aldimines by providing excess ammonia and shifting the equilibrium shown in Step 1 in Scheme 1 to the right.

The electrochemical reductive amination of the furfural-based molecules can be carried out with very high Faradaic Efficiencies (FE), where FE is defined as follows:

$$FE(\%) = \frac{\text{mol of amine formed}}{\text{Total charge passed }(C)/(F \times n)} \times 100\%, \quad (2)$$

where F is the Faraday constant (96485 C/mol) and n is the number of electrons required for the conversion of the aldimine to an amine. For example, the furfural-based molecules can be converted into amines with an FE of at least 80%. This includes embodiments of the cells and methods that produce the product amines at an FE of at least 85%, and further includes embodiments of the cells and methods that produce the product amines at an FE of at least 90%. Methods for quantifying the FE of an electrochemical reductive amination are described in the Example.

The electrochemical reductive amination of the furfural-based molecules can be carried out substantially completely to provide the reductive amination products at a high selectivity. For example, the furfural-based molecules can be converted into amines with a product selectivity of at least 70%, where selectivity is defined as follows:

$$\text{Selectivity}(\%) = \frac{\text{mol of amine formed}}{\text{mol of furfural-based molecule consumed}} \times 100\%. \quad (3)$$

This includes embodiments of the cells and methods that provide amine product selectivities of at least 80%, at least 90%, at least 95% and at least 99%. Methods for quantifying the selectivity of an electrochemical reductive amination are described in the Example.

By way of illustration only, the high Faradaic Efficiencies and amine product selectivities recited above can be achieved at or near room temperature (i.e., at temperatures in the range from about 20° C. to about 23° C.) using cell potentials in the range from about −1 to −2 V vs Ag/AgCl, as illustrated in the Example.

EXAMPLE

In this example, the catalytic ability of various metal electrodes (Ag, Cu, Pt, Sn, Zn) for reductive amination of HMF with methylamine were investigated and compared. For each metal electrode, potentials necessary to initiate reductive amination as well as potential dependent FE were investigated systematically. Ag and Zn electrodes showed an exceptional ability for reductive amination of HMF. Based on these results, optimum electrodes and reduction conditions that can achieve a FE and a selectivity nearing 100% are reported. Reductive amination of HMF derivatives such as 5-MF, DFF, and FFCA using methylamine as well as reductive amination of HMF using ethanolamine ($HOCH_2CH_2NH_2$) to establish electrochemical reductive amination as a general route for reductive amination of furfural-based biomass intermediates are also demonstrated.

A 0.7 M aqueous methylamine buffer solution (pH 11.0) containing 20 mM HMF, was prepared for electrochemical reductive amination. Aldimine formation is pH sensitive because amines go through base dissociation reaction in aqueous media and only the unprotonated base form of amine can undergo aldimine formation (Step 1 in Scheme 2). Since the $pK_a$ of $CH_3NH_3^+$ is ~10.6, adjusting the solution pH to 11 ensures a significant portion of amine to be present as a base form (0.5 M) to react with HMF to form aldimine. An NMR spectrum of 20 mM HMF in a methylamine solution (pH 11.0) shows all HMF in this solution is converted to aldimine. When the pH was lowered, the acid-base equilibrium of amine was shifted, resulting in hydrolysis of the aldimine to the aldehyde. As a result, HMF was recovered to near completion by pH 7.0.

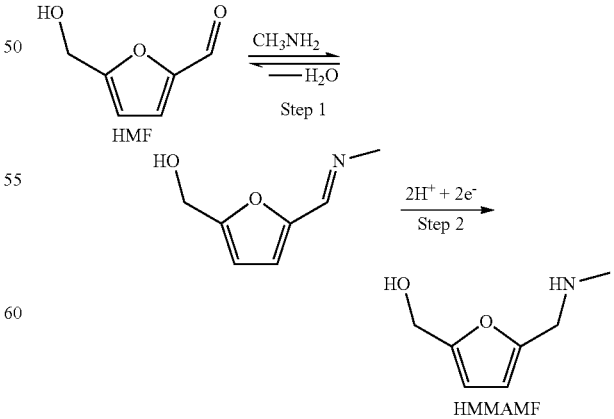

Scheme 2.

The reduction of the aldimine to the amine product, 2-hydroxymethyl-5-(methylaminomethyl)furan (HMMAMF)

(Step 2 in Scheme 2) was first examined by performing linear sweep voltammetry (LSV) using Ag, Cu, Pt, Sn, and Zn metal electrodes using methylamine solution with and without 20 mM HMF in an undivided cell (FIGS. 1A-1E). In order to maximize FE for reductive amination, metals that are known to be poorly catalytic for water reduction were investigated, except for Pt, which was chosen to serve as a control electrode. A three-electrode cell composed of one of the aforementioned metal electrodes as the cathode, a Pt anode, and a Ag/AgCl (in 4 M KCl) reference electrode was used. Cathodic current generated in the absence of HMF can be attributed to water reduction to $H_2$, as there is no other species that are reductively active. Changes to the current profile upon addition of HMF, particularly a shift in current onset to the positive direction can be considered an indication that reductive amination of HMF is favored over water reduction.

The LSVs obtained for a Pt electrode with and without HMF are shown in FIG. 1(A). When HMF was added, the cathodic onset was shifted to the negative direction with a decrease in current density. This suggests that reduction of aldimine is not favored over water reduction on Pt and aldimine adsorption on the Pt surface suppresses water reduction by blocking a portion of the active sites for $H_2$ evolution.

When Cu was used, a slight onset shift to the positive direction was observed, indicating that aldimine reduction is more favored than water reduction on Cu (FIG. 1(B)). However, cathodic current in the higher overpotential region (V>−1.41 V vs Ag/AgCl, which is equivalent to −0.56 V vs. the reversible hydrogen electrode (RHE)), where both aldimine and water reduction can occur at a considerable rate, was less than the cathodic current observed without HMF. This suggests that in this potential region, aldimine reduction is slower than water reduction and interferes with water reduction. Consequently, reduction of both aldimine and water results in a smaller current than water reduction alone.

When Cu was used, a slight onset shift to the positive direction was observed, indicating that aldimine reduction is more favored than water reduction on Cu (FIG. 1(B)). However, cathodic current in the higher overpotential region (V>−1.41 V vs Ag/AgCl, −0.56 V vs. RHE), where both aldimine and water reduction can occur at a considerable rate, was less than the cathodic current observed without HMF. This suggests that in this potential region, aldimine reduction is slower than water reduction and interferes with water reduction. Consequently, reduction of both aldimine and water results in a smaller current than water reduction alone.

When Zn was used, the most dramatic shift in cathodic current onset to the positive direction (by 250 mV) was observed upon the addition of HMF (FIG. 1(C)). Also, the cathodic current is significantly higher for all potential region when HMF is present. This shows that Zn is particularly catalytic for reductive amination of HMF.

For the case of Sn and Ag, a shift in cathodic onset of 200 mV to the positive direction was observed when HMF was added. Also, a well-defined diffusion-limited reduction peak for aldimine was observed before water reduction, which clearly confirms that HMF reduction is favored over water reduction on the Sn and Ag surface (FIGS. 1(D)-(E)). In terms of the onset potential for aldimine reduction, the Ag electrode showed the best performance as its onset for HMF reduction occurred at as early as −0.97 V vs. Ag/AgCl (−0.12 V vs RHE).

Using the LSVs as a guide for potential regions of interest, reductive amination under constant potential was performed to investigate the effect of potential on amine formation and FE. A divided cell where the cathodic compartment and the anodic compartment were divided by a glass frit was used. The cathode of interest and the Ag/AgCl reference electrode were placed in the cathode compartment while the Pt anode was placed in the anode compartment. The cathodic compartment contained 14 mL of the buffer solution (pH 11.0) with 0.02 M HMF while the anodic compartment contained the same solution without HMF. Reduction was performed by passing 20 C (or the desired coulombs) at various potentials. Results for HMF reductive amination with Ag, Cu, Sn, and Zn can be seen in Table 1. The FE and selectivity of each reaction were calculated using equations (2) and (3), where n is 2 for all substrates except DFF, where n=4.

The Pt electrode did not produce any HMF-related reduction products, suggesting that all the cathodic current generated was associated with water reduction. The Cu electrode shows a FE of 84% for aldimine reduction at −1.2 V vs. Ag/AgCl but as the potential becomes more negative, the FE for aldimine reduction gradually decreases as water reduction becomes more favorable.

The Zn, Sn, and Ag electrode showed high FE for aldimine reduction in a very wide potential region (−1.3V to −1.6 V vs. Ag/AgCl) because there is a wide window of potential where HMF reduction can occur before water reduction initiates. The most efficient condition for reductive amination in terms of FE was achieved by Zn at −1.4 V vs Ag/AgCl (−0.55 V vs RHE) with 95% FE. In fact, the FE of Zn remained near 90% to E=−1.6 V vs Ag/AgCl (−0.75 V vs RHE), at which point $H_2$ evolution becomes prevalent according to the LSVs (FIG. 1(E)). However, in terms of overpotential required, Zn was not as good as Ag. Although the maximum FE achieved by Ag was slightly less at 83%, it was achieved at −1.2 V vs. Ag/AgCl where Zn generates negligible current for aldimine reduction.

TABLE 1

Results obtained from electrochemical reductive amination of HMF by Cu, Zn, Sn, Ag, and Ag$_{gd}$ electrodes at various potentials.[a]

| Elec. Mat. | E (V) vs Ag/AgCl | FE (%) | Selectivity (%) | Average Current Density (mA/cm$^2$) | Rate of HMMAMF formation (μmol/cm$^2$min) |
|---|---|---|---|---|---|
| Cu | −1.2 | 84 | 96 | 9.02 | 0.789 |
|    | −1.3 | 71 | 65 | 14.1 | 1.04 |
|    | −1.4 | 39 | 68 | 34.2 | 1.38 |
|    | −1.5 | 26 | 69 | 46.0 | 1.22 |
| Zn | −1.3 | 82 | 85 | 9.83 | 0.831 |
|    | −1.4 | 95 | >99 | 21.6 | 2.14 |
|    | −1.5 | 94 | >99 | 28.6 | 2.77 |
|    | −1.6 | 90 | >99 | 35.9 | 3.34 |
| Sn | −1.3 | 70 | 72 | 7.08 | 0.515 |
|    | −1.4 | 94 | >99 | 21.4 | 2.08 |
|    | −1.5 | 83 | >99 | 27.9 | 2.41 |
|    | −1.6 | 77 | >99 | 37.0 | 2.96 |
| Ag | −1.1 | 79 | >99 | 6.81 | 0.558 |
|    | −1.2 | 83 | >99 | 12.2 | 1.05 |
|    | −1.3 | 68 | >99 | 18.8 | 1.33 |
|    | −1.4 | 51 | >99 | 41.0 | 2.17 |
| Ag$_{gd}$ | −1.0 | 85 | >99 | 3.86 | 0.339 |
|    | −1.1 | >99 | >99 | 18.5 | 1.91 |
|    | −1.2 | 91 | >99 | 26.7 | 2.53 |
|    | −1.3 | 83 | >99 | 33.0 | 2.83 |
|    | −1.4 | 59 | >99 | 48.8 | 2.96 |

[a]Reported values are averages obtained from three or more measurements. Reaction conditions: 0.7M methylamine buffer (pH 11.0) containing 0.02M HMF for 20 C. passed.

The selectivity of the aldimine reduction was approximately 100% for most metals and potential conditions. Cu is the notable exception, where both the FE and selectivity decreased when moving to more negative potentials. The products formed were amine dimer and oligomers. For the case of Sn and Zn, the formation of dimer and oligomer of amine was observed only in the low potential region (−1.3 V vs Ag/AgCl). All other potentials yielded HMMAMF exclusively as a conversion product of HMF.

The ideal catalytic electrode should achieve a high FE for aldimine reduction, like Zn, but require a lower overpotential, like Ag. It was demonstrated that high surface area dendritic Ag electrodes prepared by galvanic displacement of Cu (referred to as $Ag_{gd}$) (FIG. 2(A)) are particularly catalytic for electrochemical reduction of HMF to 2,5-bis (hydroxymethyl)furan (BHMF) in a pH 9.2 borate buffer solution. (See J. J. Roylance, T. W. Kim and K.-S. Choi, *ACS Catal.*, 2016, 6, 1840-1847)

While $Ag_{gd}$ is highly catalytic for reduction of HMF of BHMF, since all HMF is present as aldimine in the amine buffer solution (pH 11) used in this study, BHMF production cannot compete with reductive amination, ensuring a high FE for aldimine reduction.

Figure 2A:
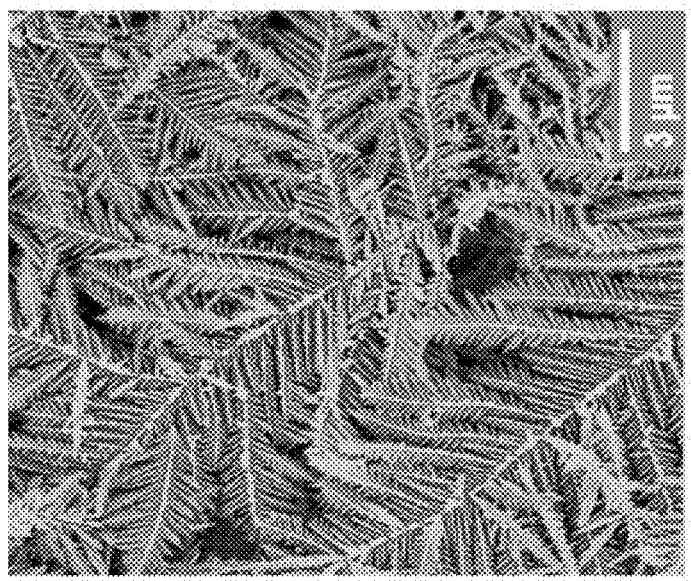
FIG. 2(A) shows a scanning electron microscope image (SEM) of an $Ag_{gd}$ electrode.

The LSVs of the $Ag_{gd}$ electrode for water and aldimine reduction is shown in FIG. 2(B) in comparison with those of the plain Ag electrode. The current onset for water reduction is −1.2 V vs Ag/AgCl (−0.35 V vs RHE) for both Ag and $Ag_{gd}$, though the current increases at a greater rate moving to more negative potentials for $Ag_{gd}$, likely due to the increased surface area. In the presence of HMF, while Ag shows the shift of onset to the positive direction by 200 mV, $Ag_{gd}$ shows the shift of onset by 300 mV, providing a wide window of overpotential where only aldimine can be reduced. The onset shift observed by $Ag_{gd}$ by adding HMF is even greater than that of Zn, which suggests that $Ag_{gd}$ is particularly catalytic for aldimine reduction.

The constant potential reduction results show that the FE for reductive amination of HMF on $Ag_{gd}$ is >99% at −1.1 V vs Ag/AgCl (−0.25 V vs RHE), which is remarkable. The FE for reductive amination decreases for E≤−1.2 V vs Ag/AgCl as $H_2$ evolution initiates. As in the case of Ag, other than $H_2$, HMMAMF was the only reduction product produced by $Ag_{gd}$, resulting in the selectivity of >99% for HMMAMF formation.

The surface morphologies of all the electrodes before and after reductive amination were imaged using SEM. No signs of surface changes were observed for the Ag, $Ag_{gd}$, and Sn electrodes. For the Cu and Zn electrodes, minor surface restructuring was observed, which should be due to the interactions with aldimine and not due to dissolution as these metals were cathodically protected during the reduction process.

Figure 3:
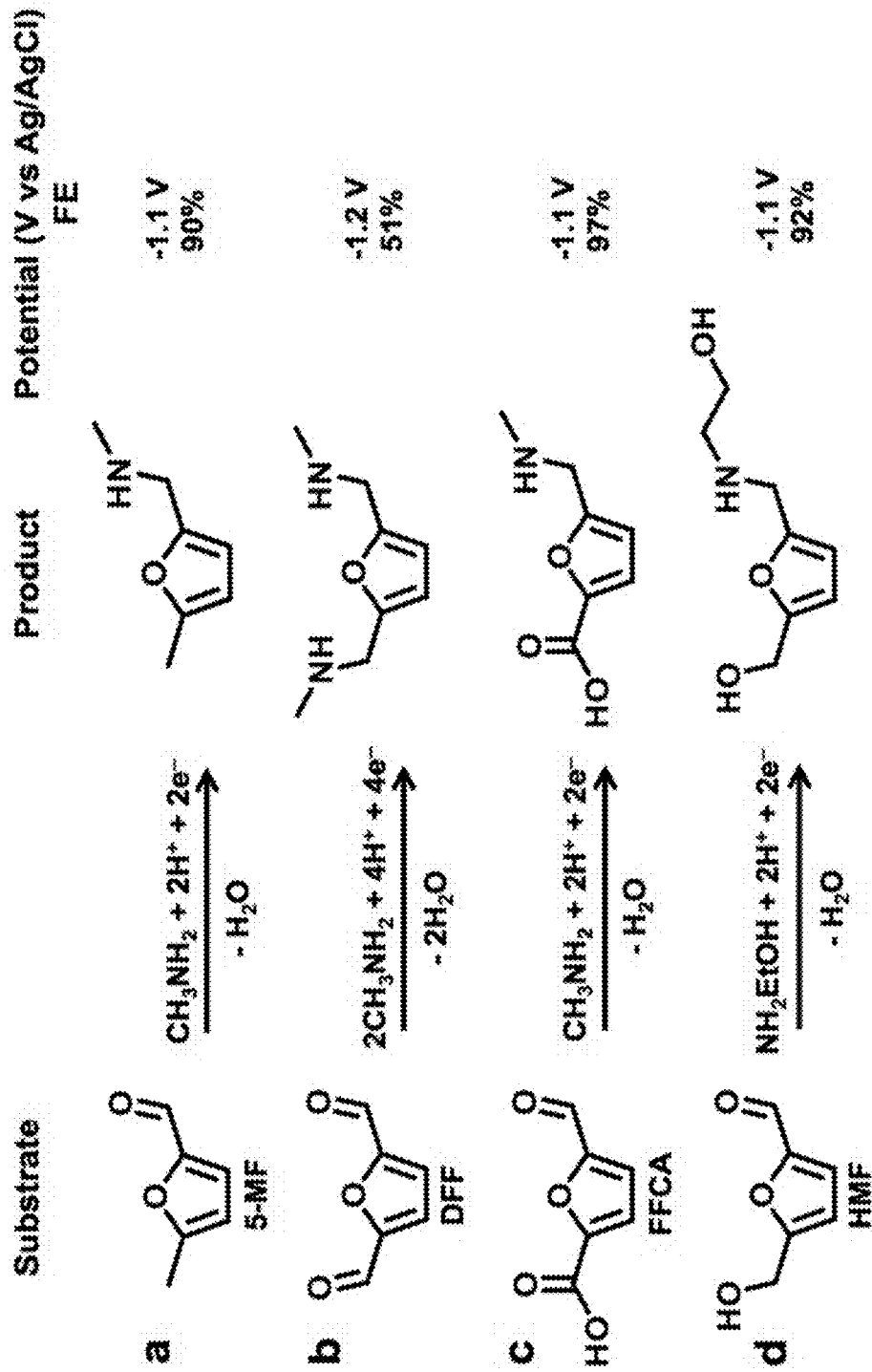
FIG. 3. Scheme (a) shows an electrochemical reductive amination of 5-methylfurfural (5-MF) with methylamine; Scheme (b) shows an electrochemical reductive amination of 2,5-diformylfuran (DFF) with methylamine; Scheme (c) shows an electrochemical reductive amination of 5-formyl-2-furancarboxylic acid (FFCA) with methylamine; Scheme (d) shows an electrochemical reductive amination of HMF with ethanolamine ($NH_2EtOH$). The potential used for reductive amination and Faradaic Efficiency for each case is also shown.

To further assess the viability of an electrochemical reductive amination, the $Ag_{gd}$ electrode was used to investigate reductive amination of various HMF-based substrates, which included 5-methylfurfural (5-MF), 2,5-diformylfuran (DFF), and 5-formyl-2-furancarboxylic acid (FFCA) (FIG. 3, Schemes (a)-(c), respectively). The reductive amination of 5-formyl-2-furancarboxylic acid results in an artificial amino acid, which could have implications in food and drug applications as well as polymer synthesis. The reductive amination product of 2,5-diformylfuran (DFF) could also have applications in polymer synthesis.

The results show that these substrates were efficiently converted to corresponding amines with high FEs (>90%). The efficiency for the reductive amination of 2,5-diformylfuran (DFF) appeared to be low with an observed FE of 51%. However, this is likely due to the low solubility of the resulting amine, as the product solution became cloudy and a small amount of precipitate could be seen after reductive amination. Judging from the fact that there are no other soluble DFF related reduction products detected by NMR analysis and that water reduction is not efficient at −1.2 V vs. Ag/AgCl, the actual FE value for the reductive amination of DFF should be much higher than the observed value.

Reductive amination of HMF using ethanolamine instead of methylamine in 0.7 M ethanolamine solution containing 20 mM HMF (FIG. 3, Scheme (d)) was also tested. The use of ethanolamine results in the addition of an alcohol group as well as an amine group, further diversifying the chemistry the product can undergo. The reductive amination of HMF with ethanolamine was found to be achieved with an FE of 92%.

The successful demonstration of reductive amination using various furfural substrates and primary amines suggests that the electrochemical conditions and catalytic electrodes reported in this study can be used as a general approach for electrochemical reductive amination of biomass intermediates. The $Ag_{gd}$ electrode was identified as an ideal electrode, which achieved the highest FE and selectivity with a minimum overpotential necessary. The use of water as the hydrogen source at ambient temperatures without requiring chemical reducing agents will decrease the cost and environmental concerns associated with conventional reductive amination.

EXPERIMENTAL

Materials.

Zinc foil (0.25 mm thick, 99.98%), Sn foil (0.025 mm thick, 99.9%), and silver nitrate (99.9+%) were purchased from Alfa Aesar. Copper foil (1 Mil, 0.001 in. thick, 99.9%) was purchased from Nimrod Hall Copper Foil Company. Sulfuric acid (95-98%), methylamine (40 wt %), ethanolamine (>99%), 5-hydroxymethylfurfural (≥99%), 5-methylfurfural (99%), dimethylsulfone, (98%), and sodium acetate (≥99.0%) were purchased from Sigma Aldrich. 2,5-diformylfuran (>98%) and 5-formyl-2-furancarboxylic acid (>98%) were purchased from TCI. All chemicals were used without further purification.

Preparation of Electrodes.

Cu, Sn, and Zn electrodes used in this study were prepared by cutting the foil to pieces with dimensions of 1.5 cm×2.5 cm. The Zn surface was mechanically polished with sandpaper. The Cu and Sn surfaces were first rinsed with 2-propanol and water, then cleaned by immersing in 1 M HCl for 1 minute to remove surface oxides. After rinsing with DI water and drying, Cu tape was attached to the foil electrodes to enable connection to the potentiostat lead. The backside and top 0.5 cm of the foil electrodes were then covered with Teflon tape to yield a 3.0 $cm^2$ working area. The cleaning and preparation of electrodes were performed immediately before use in experiments. Ag electrodes were prepared by placing clean Cu foil, cleaned using aforementioned procedures, in a sputter coater (Anatech USA, DC/RF Dual Source Sputtering System) where 100 nm of Ag was sputter-coated onto the Cu substrate. The films were then made into electrodes in the same manner as for the foil electrodes. The Pt working (1.5 cm×2.0 cm) and counter electrodes (2.5 cm×2.0 cm) were prepared by sputter coating a 100 nm platinum layer over a 20 nm titanium layer onto cleaned glass slides. Cu and Teflon tapes were then attached to the top of the Pt in the same manner as for the other electrodes. High surface area Ag electrodes ($Ag_{gd}$) were prepared by galvanic displacement by immersing clean Cu foil electrodes (1.5 cm×2.0 cm working area), cleaned and prepared just prior to deposition using the aforementioned procedures, into a 50.0 mM solution of $AgNO_3$ for 30 seconds. See J. J. Roylance, T. W. Kim and K.-S. Choi, *ACS Catal.*, 2016, 6, 1840-1847. Following deposition, the film was rinsed gently with water and dried in an air stream.

Solution Preparation and Aldimine Formation.

The 0.7 M methylamine buffer solution was prepared by diluting concentrated aqueous $CH_3NH_2$ ($pK_a$=10.6) with ultrapure water and acidifying to pH 11.0 with concentrated $H_2SO_4$. The necessary amount of HMF, 5-MF, DFF, or FFCA was added to make a 0.02 M solution. The same procedure was followed for reaction of HMF with ethanolamine ($HOCH_2CH_2NH_2$), where the solution was prepared with ethanolamine instead of methylamine. Although the $pK_a$ (9.5) of ethanolamine is lower than that of methylamine, the pH of the ethanolamine solution was adjusted to 11 to be consistent with the pH of the methylamine solution used in this study.

Reduction of HMF.

LSVs were performed in a 0.7 M methylamine buffer solution (pH 11.0) with and without 0.02 M HMF in an undivided three-electrode cell without stirring. The potential was swept from the open circuit potential to the negative direction using a scan rate of 5 mV/s. The constant potential reduction of HMF was performed in a divided cell where the cathodic compartment and the anodic compartment were divided by a glass frit. The cathodic compartment contained 14 mL of the buffer solution (pH 11.0) with 0.02 M HMF while the anodic compartment contained the same solution without HMF. Reduction was performed by passing 20 C (or the desired coulombs) at various potentials. The FE and selectivity of each reaction were calculated using equations (2) and (3), where F is the Faraday constant (96485 C/mol) and n is the number of electrons required for the conversion of the aldimine to an amine, which is 2 for all substrates except DFF, where n=4.

Product Analysis.

Products were detected and quantified via $^1H$ nuclear magnetic resonance (NMR) spectroscopy using a Bruker Avance III 400 MHz NMR spectrometer. An internal standard of dimethyl sulfone or sodium acetate was used to determine product concentrations. The HMF signal in the product solution was also compared to that of the initial solution to determine the amount of HMF consumed. The identities of the products were further confirmed by $^{13}C$-NMR, and $^1H$-$^{13}C$ HSQC. Since the water suppression method used to analyze the sample also results in a suppression of the signals near water (4.7 ppm), the product was extracted with $CDCl_3$ and analyzed to confirm peak assignments and product identification.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for the electrochemical reductive amination of furfural-based molecules to aminated furfural-based molecules in an electrochemical cell comprising an aqueous electrolyte solution, a cathode that is catalytically active for the reductive amination of aldimine intermediate molecules, and an anode in electrical communication with the cathode, wherein the electrochemical cell is either an undivided cell in which the anode and cathode are both in the aqueous electrolyte solution or a divided cell in which the cathode is in the aqueous electrolyte solution, the anode is in an anode electrolyte solution and the aqueous electrolyte solution is separated from the anode electrolyte solution by a divider, the method comprising:
   combining the furfural-based molecules with a primary amine or ammonia in the aqueous electrolyte solution,
   adjusting the pH of the aqueous electrolyte solution, such that the amount of the unprotonated form of the primary amine or ammonia is greater than the amount of furfural-based molecules and the furfural-based molecules react with the unprotonated form of the primary amine or ammonia to form the aldimine intermediate molecules; and
   creating a potential difference between the anode and the cathode to provide a flow of electrons from the anode to the cathode, wherein the electrons at the cathode and H+ from water in the aqueous electrolyte solution undergo reductive amination reactions with the aldimine intermediate molecules to form the aminated furfural-based molecules.

2. The method of claim 1, wherein the aminated furfural-based molecules are formed with a selectivity of at least 80% and a Faradaic efficiency of at least 80%.

3. The method of claim 2, wherein the cathode is a zinc cathode.

4. The method of claim 2, wherein the cathode is a tin cathode or a copper cathode.

5. The method of claim 2, wherein the cathode is a silver cathode, an indium cathode, a copper cathode, or a tin cathode and the pH of the aqueous electrolyte solution is selected to convert substantially all of the furfural-based molecules in the aqueous electrolyte solution into the aldimine intermediate molecules.

6. The method of claim 5, wherein the aqueous electrolyte solution is maintained at a pH of at least 11.

7. The method of claim 1, wherein the aminated furfural-based molecules are formed with a selectivity of at least 90% and a Faradaic efficiency of at least 90%.

8. The method of claim 1, wherein the aminated furfural-based molecules are formed with a selectivity of at least 99%.

9. The method of claim 1, wherein the pH of the aqueous electrolyte solution is greater than the pKa of the protonated form of the primary amine.

10. The method of claim 1, wherein the cathode is a silver electrode.

11. The method of claim 10, wherein the silver has a dendritic fractal morphology.

12. The method of claim 10, wherein the aminated furfural-based molecules are formed with a selectivity of at least 80% and a Faradaic efficiency of at least 99%.

13. The method of claim 1, wherein the cathode is an indium cathode.

14. The method of claim 1, wherein the aqueous electrolyte solution is substantially free of reducing agents and hydrogen sources other than the water.

15. The method of claim 1, wherein the furfural-based molecules are hydroxymethyl furfural molecules.

16. The method of claim 15, wherein the primary amine is methylamine.

17. The method of claim 1, wherein the furfural-based molecules are derivatives of 5-hydroxymethyl furfural.

18. The method of claim 17, wherein the primary amine is methylamine.

19. The method of claim 17, wherein the derivatives of 5-hydroxymethyl furfural are selected from 5-methylfurfural, 2,5-diformylfuran, 5-formyl-2-furancarboxylic acid, and combinations of two or more thereof.

20. The method of claim 1, wherein the electrochemical cell further comprises a reference electrode.

21. The method of claim 1, wherein the aqueous electrolyte solution further comprises an organic solvent that increases the solubility of the furfural-based molecules, the primary amine, or both relative to the solubility of the furfural-based molecules, the primary amine, or both in the absence of the organic solvent.

22. The method of claim 1, wherein the cathode is a tin electrode.

23. The method of claim 1, wherein the aqueous electrolyte solution is maintained at a pH of at least 11.

24. The method of claim 1, wherein the cathode is a silver cathode, an indium cathode, a copper cathode, or a tin cathode.

* * * * *